Figure 1:
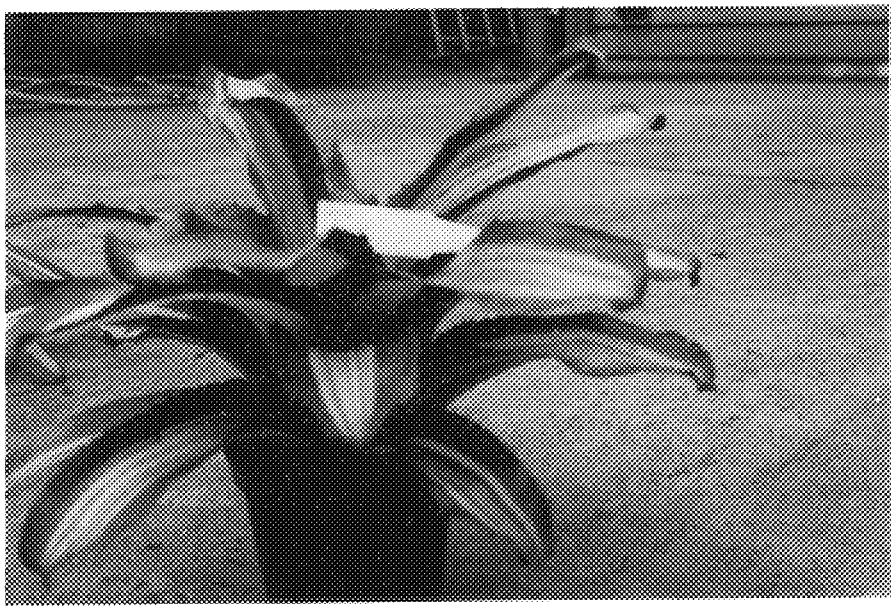

US00PP10746P

United States Patent [19]

Skotak, Jr.

[11] Patent Number: Plant 10,746

[45] Date of Patent: Jan. 5, 1999

[54] NEOREGELIA PLANT NAMED 'YANG'

[76] Inventor: Chester Skotak, Jr., APT 652, Alajuela, Costa Rica

[21] Appl. No.: 893,563

[22] Filed: Jul. 11, 1997

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

| | | | |
|---|---|---|---|
| P.P. 3,971 | 11/1976 | De Coster | Plt./88.8 |
| P.P. 7,713 | 11/1991 | Kuipers | Plt./88.8 |
| P.P. 9,597 | 7/1996 | Skotak, Jr. | Plt./88.8 |
| P.P. 9,604 | 7/1996 | Skotak, Jr. | Plt./88.8 |
| P.P. 9,627 | 8/1996 | Devroe | Plt./88.8 |

*Primary Examiner*—Howard J. Locker
*Assistant Examiner*—Kent L. Bell
*Attorney, Agent, or Firm*—Foley & Lardner

[57] ABSTRACT

A new and distinct cultivar of neoregelia plant named 'Yang', characterized by its leaves with a greenish-white center (R.H.S. 145C-D) and (R.H.S. 160A) bordered by variegation down the entire length of the leaf and a dark green margin (R.H.S. 139A); the basal portion of the innermost leaves, when in flower, is red-purple (R.H.S. 60B) and this red-purple color overlays the green and white portions of the leaves; the margins of the leaves are very serrated; and the form of the plant is a uniform rosette with long, broadly rounded apiculate, lingulate and recurved leaves.

2 Drawing Sheets

The present invention comprises a new and distinctive cultivar of Neoregelia hybrid, botanically known as Neoregelia and hereinafter referred to by the name 'Yang'.

Neoregelia species are tank epiphytes with stemless inflorescences and flowers that barely rise above the water in the center of the plants. 'Yang' can be advantageously grown as a single pot plant in order to display its symmetrically rosette plant form.

The new cultivar is a product of a planned breeding program, and was originated from a cross made by the inventor Chester Skotak, Jr. during such program in Balsa, Costa Rica in 1988. The female or seed parent was an unidentified plant of *Neoregelia carolinae lineata.* The male or pollen parent was an unidentified plant of *Neoregelia carcharodon.*

'Yang' was discovered and selected as a flowering plant within the progeny of the stated cross by Chester Skotak, Jr. in 1991 in a controlled environment in a nursery in Balsa, Costa Rica.

Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity, and day length, without, however, any variation in the genotype of the plant.

The following traits have been repeatedly observed and are determined to be basic characteristics of 'Yang' which in combination distinguish this Neoregelia as a new and distinct cultivar:

1. The center of each leaf is greenish-white (R.H.S. 145C-D) and (R.H.S. 160A) bordered by variegation down the entire length of the leaf and a dark green margin (R.H.S. 139A).

2. The basal portion of the innermost leaves, when in flower, is red-purple (R.H.S. 60B) and this red-purple color overlays the green and white portions of the leaves.

3. The margins of the leaves are very spiny.

4. The form of the plant is a uniform rosette with long, broadly rounded apiculate, lingulate and recurved leaves.

The new variety Neoregelia 'Yang' can be compared to plants of the species *Neoregelia carcharodon.* 'Yang' has a well-developed rosette of leaves and is more compact than *Neoregelia carcharodon.* The center color of the leaves when in flower flushes to a nice red-purple unlike the true species of *Neoregelia carcharodon*, which has no center color when in flower.

In the photographic drawings, FIGURE 1 comprises a side perspective view of a typical plant of the new cultivar.

Figure 2:
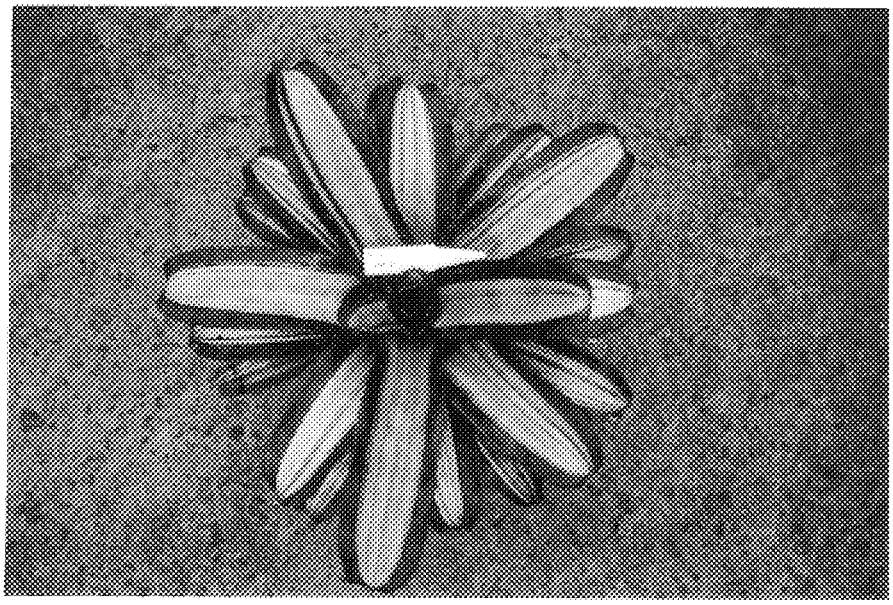

The photograph comprising FIGURE 2 is a top view of the plant. p The following observations, measurements and values describe plants grown in Balsa, Costa Rica and Apopka, Fla., under greenhouse conditions which closely approximate those generally used in horticultural practice. Color references are made to The Royal Horticultural Society (R.H.S.) Colour Chart, except where general color terms of ordinary significance are used.

Classification:

*Botanical.*—Neoregelia hybrid, cv. 'Yang'.

*Commercial.*—Neoregelia 'Yang'.

Parentage:

*Male parent.—Neoregelia carcharodon.*

*Female parent.—Neoregelia carolinae lineata.*

Propagation: Vegetative by removal of offsets.

*Form.*—From 30 to 40 cm tall when grown in 16.5 cm pots and approximately 90 cm or more in overall diameter when fully grown.

*Growth habit.*—Spreading rosette.

Leaves:

*Shape.*—Blades lingulate, recurved, broadly rounded and apiculate. Marginal spines to 5 mm.

*Size.*—Length about 50–60 cm; width is 5 cm at tip and approximately 10 cm at middle.

*Margin.*—Spiny. Spines up to 5 mm.

*Surface texture.*—Slightly coarse.

*Veins or ribs.*—None.

*Color (R.H.S.).*—Upper surface: Dark green margin (139B) and greenish-white center (145C-D and 160A) bordered by variegation down the entire length of the leaf. The innermost leaves are overlayed with red-purple (60B) and hold their color for approximately 4 to 6 months at the time of flowering. Lower surface: Minute apressed scales.

*Number of leaves.*—Average 20–25.

Rosette:

*Leaves forming the socket.*—The socket is about 4 cm in overall diameter.

*Color.*—Red-purple 60B, with the socket leaves holding their color for approximately 4 to 6 months at the time of flowering.

*Flowers.*—Arrangement: Deeply sunken rosette, simple and many flowered. Color: Petal apex violet-blue 91B with white base. Fruit: White, ovary slenderly ellipsoid and approximately 15 mm long. Duration of the flowers: Individual flowers last one day but flowering is continuous for 7 to 8 weeks.

Reproductive organs:

*Stamens.*—Pale yellow.

*Pistils.*—White; ovary is slenderly ellipsoid and approximately 15 mm long and 7 mm in diameter.

Disease resistance: Good resistance to fungi and insects exhibited in Costa Rica.

General observations: 'Yang' produces large numbers of offsets. Individual plants may produce up to 15 offsets per mature plant.

I claim:

1. A new and distinct neoregelia plant named 'Yang', as illustrated and described.

* * * * *